United States Patent [19]

Cappello et al.

[11] Patent Number: 5,427,937
[45] Date of Patent: Jun. 27, 1995

[54] HOOKWORM ANTICOAGULANT

[76] Inventors: Michael Cappello, 401 Whitney Ave., New Haven, Conn. 06511; Peter J. Hotez, 55 Buttonwood Cir., Cheshire, Conn. 06410; Frank F. Richards, 24 Huntington St., New Haven, Conn. 06511; John M. Hawdon, 91 Florence Rd., Branford, Conn. 06405

[21] Appl. No.: 55,988

[22] Filed: Apr. 30, 1993

[51] Int. Cl.[6] .......................... C12N 9/48; C12N 9/74; A61K 38/00
[52] U.S. Cl. .................................... 435/212; 435/214; 514/12
[58] Field of Search ................... 435/212, 219; 514/12

[56] References Cited

PUBLICATIONS

Capello et al. "Ancylostoma Factor Xa..." J. Inf. Dis. vol. 167 pp. 1474–1477 Jun., 1993.

*Primary Examiner*—Robert A. Wax
*Assistant Examiner*—Hyosuk Kim
*Attorney, Agent, or Firm*—Mary M. Krinsky; St. Onge Steward Johnston & Reens

[57] ABSTRACT

A soluble anticoagulant protein isolated and purified from Ancylostoma hookworms markedly prolongs both the prothrombin time and partial thromboplastin time in clotting assays. The protein has an apparent molecular weight of about 6500 daltons and exhibits amino acid sequence homology to the Kunitz-type serine protease inhibitor family. Chromogenic peptide substrate and clotting time assays indicate that the protein inhibits extrinsic pathway clotting factor VIIa, the enzyme responsible for initiating the human coagulation cascade, and factor Xa in the common pathway of the coagulation cascade.

5 Claims, 4 Drawing Sheets

SEQUENCE LISTING ( 1 ) GENERAL INFORMATION:

( i i i ) NUMBER OF SEQUENCES: 7:

( 2 ) INFORMATION FOR SEQ ID NO: 1:

( i ) SEQUENCE CHARACTERISTICS:
        ( A ) LENGTH: 58 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: internal fragment ( i x ) FEATURE:
        ( A ) NAME/KEY: pancreatic trypsin inhibitor ( x ) PUBLICATION INFORMATION:
        ( A ) AUTHORS: Ponte, P., et al.
        ( B ) TITLE: m RNA contains domain
            homologous to serine proteinase inhibitors
        ( C ) JOURNAL: Nature
        ( D ) VOLUME: 331
        ( F ) PAGES: 525-527, Figure 1
        ( G ) DATE: 11 February 1988
        ( K ) RELEVANT RESIDUES IN SEQ ID NO: segment corresponding to
            polypeptide residues 287 to 344

( x i ) SEQUENCE DESCRIPTION: SEQ ID NO: 1:

Arg Pro Asp Phe Cys Leu Glu Phe Phe Tyr Thr Gly Pro Cys Lys

|   |   |   | 290 |   |   |   |   | 295 |   |   |   |   | 300 |   |
|---|---|---|---|---|---|---|---|---|---|---|---|---|---|---|

Ala Arg Ile Ile Arg Tyr Phe Tyr Asn Ala Lys Ala Gly Leu Cys
            305             310             315

Gln Thr Pro Val Tyr Gly Gly Cys Arg Ala Lys Arg Asn Asn Glu
            320             325             330

Lys Ser Ala Glu Asn Cys Met Arg Thr Cys Gly Gly Ala
            335             340

( 2 ) INFORMATION FOR SEQ ID NO: 2:

( i ) SEQUENCE CHARACTERISTICS:
        ( A ) LENGTH: 57 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: amino terminus ( i x ) FEATURE:
        ( A ) NAME/KEY: green mamba venom serine protease
            inhibitor, delta Da-TX ( x ) PUBLICATION INFORMATION:
        ( A ) AUTHORS: Benishin, C.G.
        ( B ) TITLE: Four Polypeptide Components
            of Green Mamba Venom
        ( C ) JOURNAL: Molecular Pharmacology
        ( D ) VOLUME: 3
        ( F ) PAGES: 152-159, Figure 8
        ( G ) DATE: 1988
        ( K ) RELEVANT RESIDUES IN SEQ ID NO: numbered relative to
            alpha- DaTX ( x i ) SEQUENCE DESCRIPTION: SEQ ID NO: 2:

Ala Ala Lys Tyr Cys Lys Leu Pro Val Arg Tyr Gly Pro Cys Lys
            5               10              15

Lys Lys Ile Pro Ser Phe Tyr Tyr Lys Trp Lys Ala Lys Gln Cys
            20              25              30

Leu Pro Phe Asp Tyr Ser Gly Cys Gly Gly Asn Ala Asn Arg Phe
            35              40              45

Lys Thr Ile Glu Glu Cys Arg Arg Thr Cys Val Gly
            50              55

( 2 ) INFORMATION FOR SEQ ID NO: 3:

( i ) SEQUENCE CHARACTERISTICS:
        ( A ) LENGTH: 51 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: internal fragment ( i x ) FEATURE:
        ( A ) NAME/KEY: Extrinsic Pathway Inhibitor, Tail I ( x ) PUBLICATION INFORMATION:
        ( A ) AUTHORS: Rapaport, S.I.
        ( B ) TITLE: The Extrinsic Pathway
            Inhibitor
        ( C ) JOURNAL: Thrombosis and Haemostasis
        ( D ) VOLUME: 66
        ( E ) ISSUE: 1
        ( F ) PAGES: 6-15, Figure 5
        ( G ) DATE: 1991
        ( K ) RELEVANT RESIDUES IN SEQ ID NO: segment corresponding to
            peptide residues 26 to 76

( x i ) SEQUENCE DESCRIPTION: SEQ ID NO: 3:

Cys Ala Phe Lys Ala Asp Asp Gly Pro Cys Lys Ala Ile Met Lys
                30              35                  40

Arg Phe Phe Phe Asn Ile Phe Thr Arg Gln Cys Glu Glu Phe Ile
                45              50                  55

Tyr Gly Gly Cys Glu Gly Asn Gln Asn Arg Phe Phe Ser Leu Glu
                60              65                  70

Glu Cys Lys Lys Met Cys
                75

( 2 ) INFORMATION FOR SEQ ID NO: 4:

( i ) SEQUENCE CHARACTERISTICS:
        ( A ) LENGTH: 51 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: internal fragment ( i x ) FEATURE:
        ( A ) NAME/KEY: Extrinsic Pathway Inhibitor, Tail II ( x ) PUBLICATION INFORMATION:
        ( A ) AUTHORS: Rapaport, S.I.
        ( B ) TITLE: The Extrinsic Pathway
            Inhibitor
        ( C ) JOURNAL: Thrombosis and Haemostasis
        ( D ) VOLUME: 66
        ( E ) ISSUE: 1
        ( F ) PAGES: 6-15, Figure 5
        ( G ) DATE: 1991
        ( K ) RELEVANT RESIDUES IN SEQ ID NO: segment corresponding to
            peptide residues 98 to 148

( x i ) SEQUENCE DESCRIPTION: SEQ ID NO: 4:

Cys Phe Leu Glu Glu Asp Pro Gly Ile Cys Arg Gly Tyr Ile Thr
                100             105                 110

Arg Tyr Phe Tyr Asn Asn Gln Thr Lys Gln Cys Glu Arg Phe Lys
                115             120                 125

Tyr Gly Gly Cys Leu Gly Asn Met Asn Asn Phe Glu Thr Leu Glu
                130             135                 140

Glu Cys Lys Asn Ile Cys
                145

( 2 ) INFORMATION FOR SEQ ID NO: 5:

( i ) SEQUENCE CHARACTERISTICS:
        ( A ) LENGTH: 51 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( v ) FRAGMENT TYPE: internal fragment ( i x ) FEATURE:
        ( A ) NAME/KEY: Extrinsic Pathway Inhibitor, Tail III ( x ) PUBLICATION INFORMATION:
        ( A ) AUTHORS: Rapaport, S.I.
        ( B ) TITLE: The Extrinsic Pathway
            Inhibitor
        ( C ) JOURNAL: Thrombosis and Haemostasis
        ( D ) VOLUME: 66
        ( E ) ISSUE: 1

```
            (F) PAGES: 6-15, Figure 5
            (G) DATE: 1991
            (K) RELEVANT RESIDUES IN SEQ ID NO: segment corresponding to
                peptide residues 190 to 240

(xi) SEQUENCE DESCRIPTION: SEQ ID NO: 5:

Cys  Leu  Thr  Pro  Ala  Asp  Arg  Gly  Leu  Cys  Arg  Ala  Asn  Glu  Asn
190                      195                     200

Arg  Phe  Tyr  Tyr  Asn  Ser  Val  Ile  Gly  Lys  Cys  Arg  Pro  Phe  Lys
205                      210                     215

Tyr  Ser  Gly  Cys  Gly  Gly  Asn  Glu  Asn  Asn  Phe  Thr  Ser  Lys  Gln
220                      225                     230

Glu  Cys  Leu  Arg  Ala  Cys
235                      240

(2) INFORMATION FOR SEQ ID NO: 6:

(i) SEQUENCE CHARACTERISTICS:
            (A) LENGTH: 5 residues
            (B) TYPE: amino acid
            (C) STRANDEDNESS: single
            (D) TOPOLOGY: linear (ii) MOLECULE TYPE:
            (A) DESCRIPTION: peptide (v) FRAGMENT TYPE: internal fragment (vi) ORIGINAL SOURCE:
            (A) ORGANISM: Ancylostoma caninum
            (C) INDIVIDUAL ISOLATE: purified protein
            (D) DEVELOPMENTAL STAGE: adult hookworm (ix) FEATURE:
            (A) NAME/KEY: hookworm anticoagulant peptide (xi) SEQUENCE DESCRIPTION: SEQ ID NO: 6:
                    Tyr  Gly  Pro  Cys  Lys
                                      5

(2) INFORMATION FOR SEQ ID NO: 7:

(i) SEQUENCE CHARACTERISTICS:
            (A) LENGTH: 10 residues
            (B) TYPE: amino acid
            (C) STRANDEDNESS: single
            (D) TOPOLOGY: linear (ii) MOLECULE TYPE:
            (A) DESCRIPTION: peptide (v) FRAGMENT TYPE: internal fragment (vi) ORIGINAL SOURCE:
            (A) ORGANISM: Ancylostoma caninum
            (C) INDIVIDUAL ISOLATE: purified protein
            (D) DEVELOPMENTAL STAGE: adult hookworm (ix) FEATURE:
            (A) NAME/KEY: hookworm anticoagulant peptide (xi) SEQUENCE DESCRIPTION: SEQ ID NO: 7:

Tyr  Pro  Glu  Cys  Gly  Glu  Asn  Cys  Gly  Leu
                    5                        10
```

HOOKWORM ANTICOAGULANT

TECHNICAL FIELD OF THE INVENTION

This invention relates to an anticoagulant isolated from hookworms.

BACKGROUND OF THE INVENTION

Hookworms are intestinal nematodes that infect over 1 billion persons worldwide, with a higher prevalence in children than in adults (briefly reviewed in *Cecil's Textbook of Medicine*, 19th ed., W. B. Saunders Co., 1992, page 2010). These individuals suffer from intestinal hemorrhage as a direct consequence of blood loss caused by the adult hookworms attached to the mucosa. Hookworm disease is most common in tropical and less developed countries, where environmental and socioeconomic conditions including warm, moist soil, lack of public sewage disposal systems and the habit of walking barefoot especially favor transmission. Although other routes of infection are known, such as lactogenic transfer of larvae to infants and use of soiled bedding and clothing (Hotez, P. J., *Pediatr. Infect. Dis. J.*, 8: 516–520 (1989)), infection often occurs when exposed skin maintains contact for several minutes with soil contaminated with parasite eggs containing viable larvae. These penetrate the skin and journey to the lungs to develop into adults that eventually make their way to the upper small intestine, where they attach to the mucosa.

Hookworm disease is due primarily to gastrointestinal blood loss and attendant iron deficiency anemia. Adult worms attached to the mucosa digest ingested blood as well as cause focal bleeding. Each hookworm can suck as much as 0.2 ml of blood per day (Spellman, G. G., and Nossel, H. L., *Amer. J. Phys.* 220: 922-927 (1971)). This dramatic blood loss can reduce peripheral hemoglobin concentrations to as low as 3 g/100 ml. More commonly, however, blood loss is insidious, and results in chronic iron-deficiency anemia. Thus, in its human host, the adult hookworm functions as a conduit that empties blood into the intestinal tract, producing blood loss on a global scale equivalent to the exsanguination of 1.5 million people per day (Hotez, cited above). Nutritional deficiencies secondary to coexisting conditions that result in low iron stores contribute to morbidity.

The remarkable ability of a single small parasite to cause so much blood loss raises the question of an effective anticoagulating mechanism. Loss of blood from the gastrointestinal tract would be facilitated if the ability of blood to clot were impaired in persons infected with this parasite. Early in this century, researchers observed that extracts of the dog hookworm contained a substance that delayed coagulation of human blood (Loeb, L., and Fleisher, M. S., *J. Infect. Dis.* 7: 625–631 (1910)). Some fifty years later, it was subsequently noted that hookworm protein, when added to mammalian plasma, markedly prolongs both the prothrombin and partial thromboplastin times (Spellman and Nossel, cited above, and Carroll, S. M., et al., *Thromb. Haemostas.* 51: 222–227 (1984)).

Although some of this effect has been attributed to a fibrinogenolytic and fibrinolytic protease that degrades fibrinogen (Hotez, P. J., et al., *J. Biol. Chem.* 260: 7343–7348 (1985)), the exact location in the clotting cascade at which the predominant anticoagulant effect is exerted has not been determined. One investigator reported that extracts of hookworm cephalic glands, while significantly prolonging the prothrombin time, had no appreciable effect on the Stypven-activated factor X clotting time; the anticoagulant was characterized as a protein with a molecular weight between 20,000 and 50,000 daltons (Eiff, J. A., *J. Parasitol.* 52: 833–843 (1966)). Other investigators, on the other hand, demonstrated that extracts of the whole worms did, in fact, prolong the Stypven time, arguing in favor of the presence of an inhibitor of factor Xa (Spellman and Nossel, cited above).

Blood coagulation, initiated by substances in injured tissues, is propagated by an interlocking network of enzymatic activation, propagation, and control events, the so-called coagulation cascade. These complex reactions ensure that blood coagulation happens quickly and yet remains localized. Blood coagulation results in the formation of a protein scaffolding, the fibrin clot, that controls bleeding and serves as a nidus for subsequent cellular ingrowth and tissue repair. After several days, the fibrin clot is lysed and replaced with a more permanent scaffolding of connective tissue matrix molecules. Abnormalities that result in delay of clot formation or premature lysis of clots are associated with a bleeding tendency.

Coagulation and fibrinolysis involve many blood plasma proteins (see, for example, Table 155-1 in Cecil, cited above, page 1000), with the list growing longer as blood coagulation mechanisms are studied in greater detail. Structural and functional similarities can be employed to group the proteins. For example, one group are zymogens of serine proteases, and hence members of the serine protease family of proteins which includes trypsin, chymotrypsin, elastase, plasmin and cathepsin G. In the coagulation cascade, Factors II, VII, IX, X, XI, XII and protein C are in the serine protease family. These are modified by a vitamin K-dependent posttranslational carboxylation of glutamic acid residues, which allows the proteins to bind calcium and phospholipids and thereby participate efficiently in blood coagulation. Tissue plasminogen activator in the coagulation cascade is also a serine protease. Other proteins are Serine protease inhibitors and hence members of the "serpin" family of proteins, which includes antithrombin III, heparin cofactor II, and plasminogen activator.

Blood coagulation can be initiated by exposure of blood to tissue factor, the so-called "extrinsic system", or by activation of contact factors of plasma, the so-called "intrinsic system". Both of these initiation pathways lead to a common pathway, which results in the elaboration of thrombin, the master coagulation enzyme. Two major coagulation tests mentioned above differentiate these pathways. In the prothrombin time (herein denoted PT) test, tissue factor is added to plasma so that activation proceeds by the extrinsic pathway. In the partial thromoplastin time (herein denoted PTT) test, blood plasma is activated by the intrinsic pathway. The pathways are related somewhat because deficiencies of Factor IX, an intrinsic factor, as well as the factors that follow Factor IX in the intrinsic and common pathways and Factor VII, an extrinsic factor that activates IX and X, are all associated with a bleeding tendency. In contrast, deficiency of Factor XII and prekallikrein, which activates XII, does not cause a bleeding problem.

SUMMARY OF THE INVENTION

It is an object of the invention to provide a new anticoagulant.

It is a further and more specific object of the invention to provide an anticoagulant that can be used as a therapeutic agent for the treatment of numerous vascular disorders, as well as for the development for vaccines for hookworm infection and strategies for lessening the sequelae of chronic infection.

These and other objects are accomplished by the present invention which provides a soluble protein anticoagulant isolated and purified from Ancylostoma, particularly Ancylostoma caninum, hookworms. In clotting assays, the protein prolongs the prothrombin time and partial thromboplastin time. It inhibits clotting factors VIIa, the enzyme responsible for initiating the human clotting cascade, and Xa, thus exhibiting common pathway inhibitory activity as well. The protein does not inhibit thrombin or clotting factors II and V.

The protein has an apparent molecular weight of about 6500 daltons. It contains the amino acid sequence Tyr-Pro-Glu-Cys-Gly-Glu-Asn-Cys-Gly-Leu, thus exhibiting sequence homology with polypeptides belonging to the Kunitz-type family of serine protease inhibitors.

The invention also provides DNA encoding the hookworm anticoagulant, biologically functional circular plasmid or viral DNA vectors comprising the DNA, and procaryotic or eucaryotic host cells such as E. coli. transformed or transfected with the vectors in a manner allowing the host cell to express the protein.

DESCRIPTION OF THE FIGURERS

FIG. 1 shows selective inhibition by hookworm extract of the chromogenic hydrolysis of substrate (40 ug Chromozym X) by 0.01 units of purified factor Xa (open bars). Equal amounts of hookworm protein do not inhibit the activity of purified thrombin versus its substrate (Chromozym TH, hatched bars).

FIG. 2 shows partial purification of hookworm inhibitor by Q Sepharose column chromatography. Hookworm extract from 100 adult worms was added to a 1.7×9 cm Q Sepharose column using gravity flow. A major protein peak (denoted—) was eluted .from the column with a 2.0M NaCl gradient. Individual column fractions (approximately 1 ml) were collected and assayed for factor Xa inhibitory activity by chromogenic assay (denoted--).

DETAILED DESCRIPTION OF THE INVENTION

Figure 1:
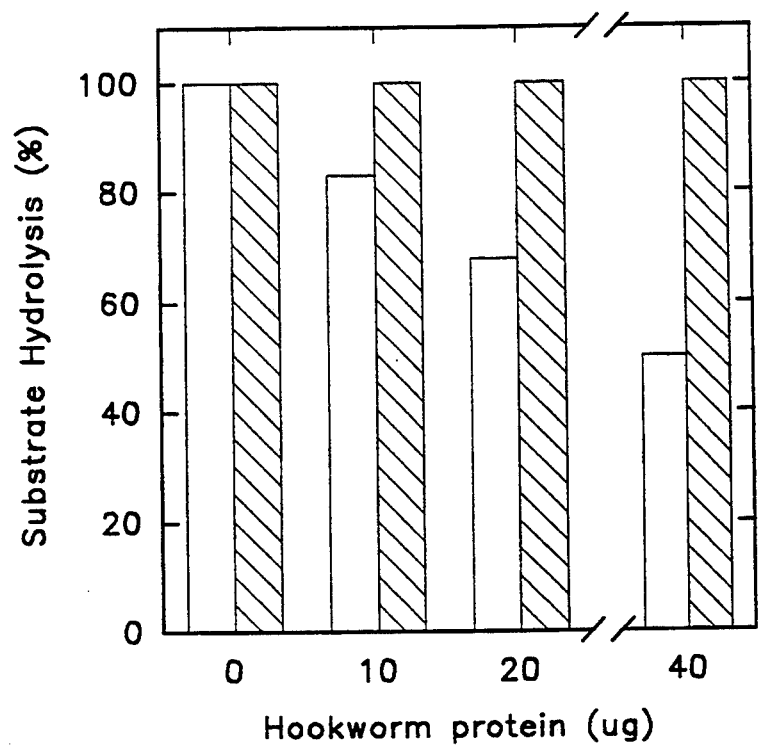

This invention is based upon the finding that a low molecular weight protein isolated and purified from hookworms binds to and inhibits both extrinsic factor VIIa, the enzyme responsible for initiation of the human coagulation cascade, and factor Xa in the common pathway.

By "hookworm" is meant any nematode that sucks blood from the small intestine including, but not limited to, the major hookworms that infect humans, *Ancylostoma duodenale, Necator americanus,* and, less commonly, *A. ceylonicum,* as well as hookworms that infect other animals such as *Ancylostoma caninum, Bunostomum phlebotomum, Agriostomum vryburgi, B. trigonocephalum, Gaigeria pachyscelis.* Other blood-sucking nematodes such as Haemonchus species, e.g., *H. contortus,* are also encompassed by this invention. *Ancylostoma caninum* is preferred in one embodiment.

In the practice of this invention, a soluble protein anticoagulant is isolated and purified from hookworms. By "purified" is meant essentially homogenous, yielding one polypeptide band on electrophoresis in a system that separates proteins; purified anticoagulant is thus substantially free of other hookworm constituents, including associated proteins. Generally, the preparation is carried out by homogenizing or lysing the nematodes to obtain soluble extracts, and purifying the protein from the extracts. Any type of protein purification scheme familiar to the skilled artesan can be employed, such as, for example, affinity, ion-exchange, exclusion, partition, liquid and/or gas-liquid chromatography; zone, paper, thin layer, cellulose acetate membrane, agar gel, starch gel, and/or acrylamide gel electrophoresis; immunochemical methods; combinations of these with each other and with other separation techniques such as dialysis; and the like.

In one embodiment, protein is obtained by separating proteins in a hookworm extract using a Sepharose ion exchange column, followed by purification on an affinity column consisting of purified human factor Xa bound to agrose resin and gel filtration through a Sepharose gel column. Experimental details are given hereinafter.

Hookworm anticoagulant protein so obtained prolongs the prothrombin time and partial thromboplastin time in clotting assays, as well as the factor X (Stypven) clotting time. It inhibits extrinsic factor VIIa, the enzyme responsible for initiating the human coagulation cascade. In addition, it is also capable of binding to factor Xa in the common pathway of the coagulation cascade. As such, it bears a striking similarity to the mammalian Extrinsic Pathway Inhibitor (EPI), a major endogenous anticoagulant produced by human tissues to regulate the coagulation cascade. Hookworm anticoagulant does not inhibit the hydrolytic activity of purified thrombin and does not inhibit clotting factors II and V.

The hookworm anticoagulant of this invention exhibits a molecular weight of about 6500 daltons. It contains the amino acid sequence Tyr-Pro-Glu-Cys-Gly-Glu-Asn-Cys-Gly-Leu, thus exhibiting sequence homology with polypeptides belonging to the pancreatic trypsin or Kunitz-type family of serine protease inhibitors (named after the first inhibitor to be isolated in crystalline form, the first for which typical 1:1 enzyme-inhibitor stoichiometry was determined, the first for which reversibility was demonstrated, the first to be sequenced, and the first to have the three-dimensional structure determined; reviewed by Laskowski, M., and Kato, I., *Ann. Rev. Biochem.* 49: 593–626 (1980)). Members of this polypeptide family have been found in many species including other mammals, snails, and sea anemones, as well as in soybeans and snake venoms. The gene coding for Kunitz type inhibitors is thus very old and very widely distributed.

Also encompassed by this invention are synthetic hookworm anticoagulants exhibiting activity and structure similar to the isolated and purified protein. Since the protein is small, it can be prepared from its constituent amino acids by sequential formation of peptide bonds using any chemical means. Alternately, the amino acid sequence can be used to prepare cloned complementary DNA sequences defining the hookworm anticoagulant of this invention, which can then be used to transform or transfect a host cell for protein expression using standard means. Also encompassed by this invention are DNA sequences homologous or closely related to complementary DNA described herein, namely DNA sequences which hybridize, particularly under stringent conditions, to hookworm anticoagulant cDNA, and RNA corresponding thereto. In addition to the anticoagulant-encoding sequences, DNA encompassed by this invention may contain additional sequences, depending upon vector construction sequences, that facilitate expression of the gene.

Because of the degeneracy of the genetic code, a variety of codon change combinations can be selected to form DNA that encodes the anticoagulant protein of this invention, so that any nucleotide deletion(s), addition(s), or point mutation(s) that result in a DNA encoding the protein are encompassed by this invention. Since certain codons are more efficient for polypeptide expression in certain types of organisms, the selection of gene alterations to yield DNA material that codes for the protein of this invention are preferably those that yield the most efficient expression in the type of organism which is to serve as the host of the recombinant vector. Altered codon selection may also depend upon vector construction considerations.

DNA starting material which is employed to form DNA coding for the hookworm anticoagulant of the invention may be natural, recombinant or synthetic. Thus, DNA starting material isolated from tissue or tissue culture, constructed from oligonucleotides using conventional methods, obtained commercially, or prepared by isolating RNA coding for anticoagulant protein, and using this RNA to synthesize single-stranded cDNA which is used as a template to synthesize the corresponding double stranded DNA can be employed to prepare DNA encoding the anticoagulant of this invention.

DNA encoding the protein of this invention, or RNA corresponding thereto, are then inserted into a vector, e.g., a pBR, pUC, pUB or pET series plasmid, and the recombinant vector used to transform a microbial host organisms. Host organisms useful in the invention are bacterial (e.g., *E. coli* or *B. subtilis*), yeast (e.g., *S. cerevisiae*) or mammalian (e.g., mouse fibroblast). This invention thus also provides novel, biologically functional viral and circular plasmid RNA and DNA vectors incorporating RNA and DNA sequences describing the hookworm anticoagulant generated by standard means. Culture of host organisms stably transformed or transfected with such vectors under conditions facilitative of large scale expression of the exogenous, vector-borne DNA or RNA sequences and isolation of the desired polypeptides from the growth medium, cellular lysates, or cellular membrane fractions yields the desired products.

The present invention thus provides for the total and/or partial manufacture of DNA sequences coding for hookworm anticoagulants, and including such advantageous characteristics as incorporation of codons preferred for expression by selected non-mammalian hosts, provision of sites of cleavage by restriction by endonuclease enzymes, and provision of additional initial, terminal or intermediate DNA sequences which facilitate construction of readily expressed vectors. Correspondingly, the present invention provides for manufacture (and development by site specific mutagenesis of cDNA and genomic DNA) of DNA sequences coding for microbial expression of anticoagulant analogues which differ from the forms specifically described herein in terms of identity or location of one or more amino acid residues (i.e., deletion analogues containing less than all of the residues specified for anticoagulant, and/or substitution analogues wherein one or more residues are added to a terminal or medial portion of the polypeptide), and which share the biological properties of hookworm anticoagulant described herein.

DNA (and RNA) sequences of this invention code for all sequences useful in securing expression in procaryotic or eucaryotic host cells of polypeptide products having at least a part of the primary structural conformation, and one or more of the biological properties of hookworm anticoagulant which are comprehended by: (a) the DNA sequences encoding anticoagulant protein as described herein, or complementary strands; (b) DNA sequences which hybridize (under hybridization conditions) to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of anticoagulants included therein, and sequences encoding RNA, fragments thereof, and analogues wherein RNA or DNA sequences may incorporate codons facilitating transcription or RNA replication of messenger RNA in non-vertebrate hosts.

Isolation and purification of microbially expressed proteins provided by the invention are by conventional means including, for example, preparative chromatographic separations such as that illustrated in the Examples, and immunological separations, including monoclonal and/or polyclonal antibody preparations.

The hookworm anticoagulant protein of this invention exhibits a number of desirable characteristics. Unlike other anticoagulants derived from blood feeding parasites such as the tick Ornithodoros moubata (Waxman, L., et al., *Science* 248: 593–596 (1990)), the blackfly *Simulium vittatum* (Jacobs, J. W., et al., Thromb. Haemost. 61: 235–238 (1989)), and two species of leeches, *Haementeria officinalis* (Nutt, E., et al., *J. Biol. Chem.* 263: 10162–10167 (1988)) and *Haementeria ghilianii* (Condra, C., Thromb. Haemost. 61: 437–441 (1989)), most of which are capable of inhibiting components of the common pathway (factor Xa and thrombin), hookworm anticoagulant binds to and inhibits the activity of clotting factor VIIa, the enzyme responsible for initiating the human coagulation cascade. Moreover, the protein of this invention is small, soluble and potent. Thus it has utility as a therapeutic agent for the treatment of numerous vascular disorders including peripheral vascular disease, stroke, coronary heart disease, hypercoagulable states, and other clotting disorders.

As the major morbidity associated with hookworm infection is a reflection of the gastrointestinal blood loss caused by the adult worm, interventions aimed at inhibiting the anticlotting mechanisms of these intestinal helminths may significantly lessen the sequelae of chronic infection. The isolation and purification of hookworm anticoagulant thus also provides a means to develop hookworm alternative therapies to prevent blood loss during infection. The isolation and purification of hookworm anticoagulant also provides a polypeptide marker for diagnostic purposes.

In addition, enhancement of an immune response aimed at the hookworm anticoagulant represents a viable strategy for vaccine development focused on reducing the burden of hookworm infection in populations at risk. Hookworm infection is one of the most clinically important soil-transmitted helminthiases, and third world children suffer most from this usually insidious hemorrhage (Hotez, cited above). As an antigen, the protein of this invention offers potential for vaccination.

The following examples are presented to further illustrate and explain the present invention and should not be taken as limiting in any regard.

EXAMPLES

Adult hookworms of the genus *Ancylostoma caninum* were obtained from the intestines of an infected dog as described by Schad, G. A., *Exp. Parasitol.* 47: 246–253 (1979). Briefly stated, infected dogs were sacrificed when they exhibited peak parasite populations (determined by counting the number of hookworm eggs per gram of feces, about 22 to 31 days post-infection). The isolated worms were stored frozen at −70° C. Crude hookworm extracts were prepared by suspending ∼100 adult worms at a time in 1 mL of 0.05M Tris-HCl buffer, pH 7.5 (hereinafter referred to as "buffer"), and grinding in a glass homogenizer for 10 minutes on ice. This suspension was then centrifuged at 8000 g for 2 minutes, and the supernatant was collected. The protein content of the extracts was then determined using Bradford's method, which involves the binding of Coomassie blue to proteins, resulting in a shift in absorption maximum of the dye (Bradford, M. M., *Anal. Biochem.* 72: 248–254 (1976)). Extracts were frozen at −20° C.

A chromogenic assay employing commercially purified human coagulation factor Xa and chromogenic substrate (Chromozym X, N-methoxycarbonyl-Nle-Gly-Arg-4-nitranilideacetate) purchased from Boehringer-Mannheim (Indianapolis) was employed to characterize the hookworm protein extracts and identify proteins subsequently purified from it. Ten ul of Factor Xa (0.01 units) were incubated with 20 ul of hookworm extracts, protein or buffer A (0.05M Tris-HCl, pH 8.2, 0.1% bovine serum albumin) for 10 minutes at 20° C. Nine hundred ul of buffer A was added, followed by 20 ul (40 ug) of Chromozym X. The mixture was allowed to react for 6 hours and optical density was then measured at 405 nm. Negative controls lacking purified factor Xa showed minimal hydrolysis under the same conditions Identical conditions were used for measuring the effect of hookworm protein on the chromogenic hydrolysis of 40 ug of substrate (Chromozym TH: Tosyl-Gly-Pro-Arg-4-nitranilide-acetate) by commercially purified human thrombin (0.02 units), both purchased from Boehringer-Mannheim.

Factor X clotting time was determined by adding 50 uL pooled human plasma to 50 uL of hookworm extracts or protein in 150 uL buffer. To 100 uL of this was added 150 uL bovine factor X-deficient plasma (Sigma, St. Louis), 100 uL of Stypven (Sigma, 1:10 dilution), cephalin (Sigma), and CaCl$_2$ (0.035M) as described by Bachmann (Bachmann, F., et al., *Thromb. Diathesis Haem.* 2: 24–38 (1958)). Time to clot was measured and compared to both standard curve and controls using buffer in the absence of hookworm protein.

As depicted in FIG. 1, factor Xa activity was reduced by 50% in the presence of 40 ug of crude soluble hookworm protein. Using the factor X clotting time bioassay, factor X clotting time was increased by 71% relative to control plasma alone in the presence of 500 ug of crude hookworm extracts.

Prothrombin time (PT) and partial thromboplastin time (PTT) were determined by adding hookworm extracts or protein to 400 uL of pooled human plasma at 20° C. and then measuring PT and PTT using Dade Thromboplastin C Plus ® Dade Actin FSL ® (Baxter Healthcare, Miami), respectively, in a MLA 1000 automatic clotting time recorder (Medical Laboratory Automation, Mount Vernon, N.Y.). Results were expressed as percentage increase in clotting times compared to controls in which buffer was substituted for hookworm protein. Using these procedures, adding 0.6 mg of crude soluble hookworm protein to 0.4 ml of human plasma, PT was prolonged by 125% (from 9.9 seconds to 22.3 seconds), and the PTT was prolonged by 57% (from 29.2 seconds to 45.9 seconds).

Figure 2:
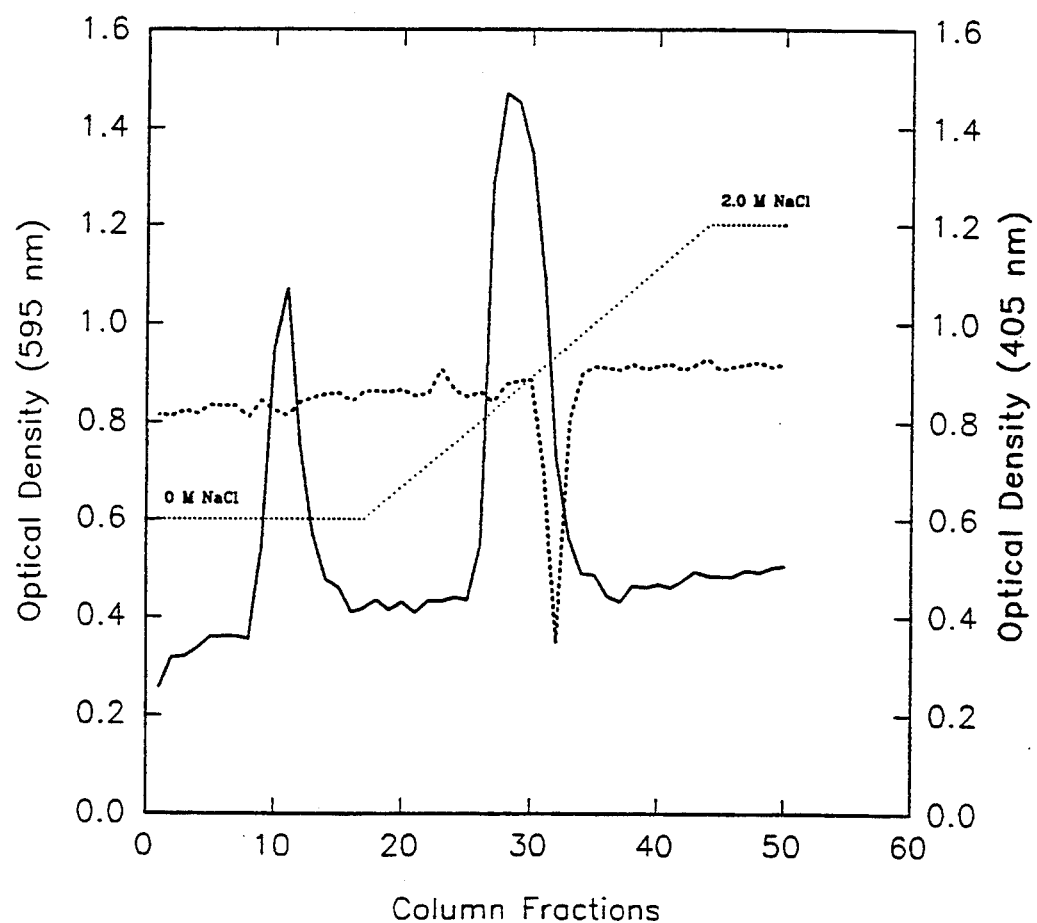

The supernatant containing soluble hookworm protein was applied to a 2.7×9 cm Q-Sepharose ion exchange column (Sigma, fast flow, wet bead size 45 to 165 u) equilibrated in buffer containing 1.0 mM orthophenanthroline, 1.0 mM dithiothreitol, 0.1 mg/ml 13,000 to 23,000 molecular weight polyvinyl alcohol, and 0.1% polyoxyethylene 23 lauryl ether (30% wt/vol). Bound protein was eluted with a 0 to 2.0M NaCl gradient, and those fractions in the elution (FIG. 2) which were capable of inhibiting factor Xa in a chromogenic assay described above were pooled and frozen.

Figure 3:
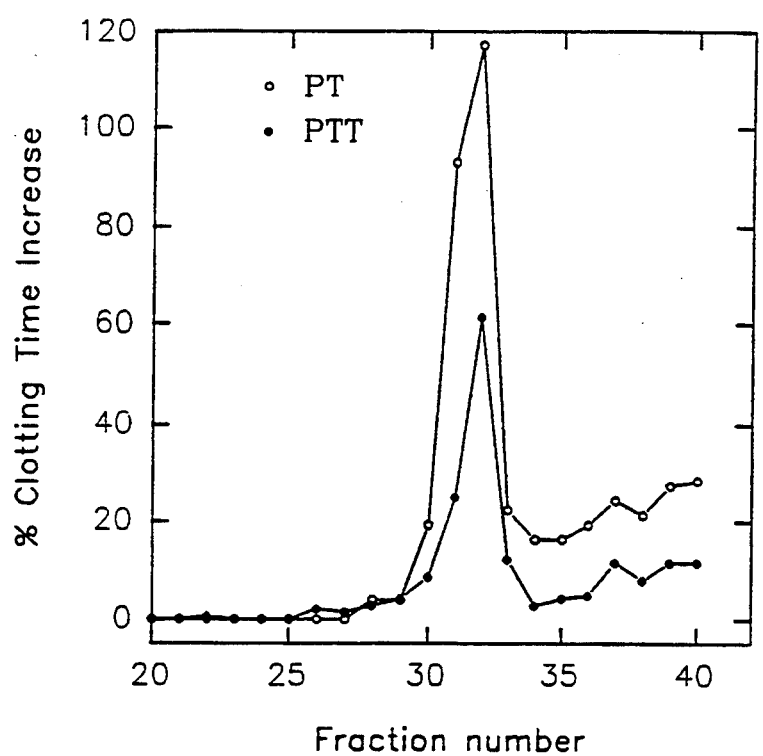
FIG. 3 shows the effect of Q Sepharose column fractions on prothrombin (open circles) and partial thromboplastin times (closed circles; control clotting times: PT=1.0 seconds, PTT=28.3 seconds). The peak of anticoagulant activity, i.e., prolongation of PT/PTT, corresponds to the peak of inhibition observed with the chromogenic assay of factor Xa activity.

The column fractions that exhibited the most significant factor Xa inhibitory activity in vitro also prolonged the factor X clotting time by 33%. Fractions were also assayed for their ability to prolong the PT and PTT. As shown in FIG. 3, the column fractions that contained the factor Xa inhibitory activity were identical to the column fractions that prolonged both the PT and PTT. No other column fractions inhibited the activity of purified factor Xa or caused prolonged of the PT/PTT.

Specific inhibition of factor Xa hydrolytic activity was enriched fivefold after Q-Sepharose, from 7.75 inhibitory units (IU)/mg of protein to 42 IU/mg of protein. One IU was defined as the amount of hookworm protein that would cause a 1% reduction in the rate of chromogenic substrate hydrolysis by purified factor Xa, compared to controls. Pooled fractions obtained from the Q-Sepharose column that inhibit factor Xa were dialized against buffer containing 0.1M NaCl and applied to an affinity column consisting of purified human factor Xa bound to agarose resin. The protein that bound to this Factor Xa was eluted with 0.17M acetic acid. Those fractions which were eluted from the column and contained factor Xa inhibitory activity were pooled, and the buffer changed to buffer containing 0.1M NaCl using a Centricon 3 ® microconcentrator (Amicon).

The pooled fractions were applied to a Superose 12 (Pharmacia) gel filtration column (24 ml) using fast pressure liquid chromatography. The fractions containing factor Xa inhibitory activity, which exhibited over a 100-fold increase over the original extract, were pooled and lyophilized. At this point, the protein was visualized as a single band on SDS-polyacrylamide gel electrophoresis under denaturing and non-denaturing conditions. The apparent molecular weight of the purified anticoagulant protein was approximately 6500 daltons.

Figure 4:
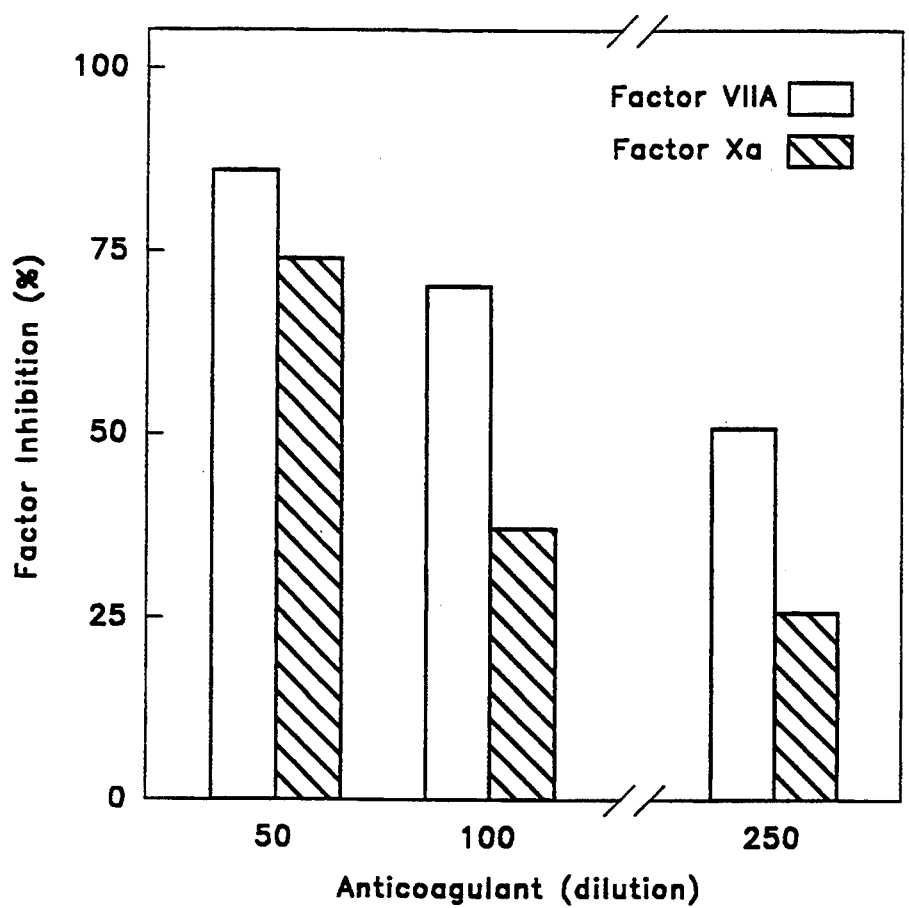
FIG. 4 shows the effect of purified hookworm anticoagulant on factors VIIa (open bars) and Xa (hatched bars ) using an in vitro chromogenic assay analogous to that described for FIG. 1 above.

Purified anticoagulant was shown to inhibit the activity of clotting factor VIIa (FIG. 4) using a procedure analogous to the one described for the assay of clotting factor Xa above, except that factor VIIa was used instead. Using the chromogenic assay described above, the protein does not appear capable of inhibiting the hydrolytic activity of purified thrombin, another serine protease in the common pathway of the coagulation cascade. Likewise, the soluble protein had no effect on factors II and V (in clotting time assays similar to the prothrombin, partial thromboplastin time assays described above).

Preliminary amino acid sequence data identified two peptide fragments, Tyr-Gly-Pro-Cys-Lys (SEQ ID NO 6) and Tyr-Pro-Glu-Cys-Gly-Glu-Asn-Cys-Gly-Leu (SEQ ID NO 7), that are set out in Table I (as item 6). Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. (Full amino acid sequences using the Patent Office format are set forth hereinafter in the Sequence Listing section of this application.)

The hookworm protein sequences exhibit homologies to pancreatic trypsin inhibitor (item 1, SEQ ID NO 1), green mamba venom (item 2, SEQ ID NO 2) and extrinsic pathway inhibitor (items 3 to 5, SEQ ID NOs 3 to 5), suggesting that the purified protein is in the Kunitz-type serine protease inhibitor family with these polypeptides.

TABLE 1

1. RPDFCLEPPYTGPCKARI I RYFYNAKAGLCQTPVYGGCRAKRNNEKS AENCMRTCGGA
2. AAKYCKLPVRYGPCKKKI PSFYYKWKAKQCLPFDYSGCGGNANRFKTI EECRRTCVG
3.         CAFKADDGPCKAIMKRFFFNI FTRQCEEFI YGGCEGNQNRFFS LEECKKMC
4.         CFLEEDPGI CRGYI TRYFYNNQTKQCERFKYGGCLGNMNNFETLEECKNI C
5.         CLTPADRGLCRANENRFYYNS VI GKCRPFKYSGCGGNENNFTS KQECLRAC
6.         YGPCK                                                  YPECGENCGL 1. pancreatic trypsin inhibitor
2. green mamba venom
3. extrinsic pathway inhibitor, tail I
4. extrinsic pathway inhibitor, tail II
5. extrinsic pathway inhibitor, tail III
6. hookworm anticoagulant The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the claims that follow. The claims are meant to cover the claimed components and steps in any sequence which is effective to meet the objectives there intended, unless the context specifically indicates the contrary.

---

We claim:

1. An anticoagulant composition comprising a purified soluble protein isolated from hookworms selected from the group consisting of *Ancylostoma duodenale, Ancylostoma ceylanicum, Necator americanus,* and *Ancylostoma caninum,* wherein said protein prolongs the prothrombin time and partial thromboplastin time, and wherein said protein inhibits clotting factor Xa, does not inhibit thrombin or clotting factors II and V, and also wherein said protein contains the amino acid sequence Tyr-Pro-Glu-Cys-Gly-Glu-Asn-Cys-Gly-Leu.

2. A composition according to claim 1 wherein said protein exhibits a molecular weight of about 6500 daltons.

3. A composition according to claim 1 wherein said protein is isolated and purified from *Ancylostoma caninum*.

4. A composition according to claim 1 wherein said protein is isolated and purified from *Necator americanus*.

5. An anticoagulant composition comprising a purified soluble protein isolated from *Ancylostoma caninum* or *Necator americanus*, wherein said protein inhibits clotting factor Xa but does not inhibit thrombin or clotting factors II and V and also wherein said protein contains the amino acid sequence Tyr-Pro-Glu-Cys-Gly-Glu-Asn-Cys-Gly-Leu.

* * * * *

UNITED STATES PATENT AND TRADEMARK OFFICE
CERTIFICATE OF CORRECTION

PATENT NO. : 5,427,937
DATED : June 27, 1995
INVENTOR(S) : Michael Cappello, et. al.

It is certified that error appears in the above-indentified patent and that said Letters Patent is hereby corrected as shown below: Title page after "References Cited" add:

Bachmann, F., et al., Thromb. Diathesis Haem. 2:24-38 (1958).
Bradford, M.M. Anal. Biochem. 72: 248-254 (1976).
Carroll, S.M., et al., Thromb. Haemostas. 51: 222-227 (1984).
Cecil's Textbook of Medicine, 19th ed., W.B. Saunders Co., 1992, pages 1000 and 2010.
Condra, C., Thromb. Haemost. 61: 437-441 (1989).
Eiff, J.A., J. Parasitol. 52: 833-843 (1966).
Hotez, P.J., Pediatr. Infect. Dis. J., 8: 516-520 (1989).
Hotez, P.J., et al., J. Biol. Chem. 260: 7343-7348 (1985).
Jacobs, J.W., et al., Thromb. Haemost. 61: 235-238 (1989) note: cited incorrectly as 61: 437-441.
Laskowski, M. and Kato, I., Ann. Rev. Biochem. 49:593-629 (1980).
Loeb, L. and Fleisher, M.S., J. Infect. Dis. 7: 625-631 (1910).
Nutt, E., et al., J. Biol. Chem. 263: 10162-10167 (1988).
Schad, G.A., Exp. Parasitol. 47: 246-253 (1979)
Spellman, G.G. and Nossel, H.L., Amer. J. Phys. 220: 922-927 (1971).
Waxman, L., et al., Science 248: 593-596 (1990).

Signed and Sealed this

Twenty-seventh Day of August, 1996

Attest:

BRUCE LEHMAN

*Attesting Officer*     *Commissioner of Patents and Trademarks*